(12) United States Patent
Shingrani et al.

(10) Patent No.: US 11,284,806 B2
(45) Date of Patent: Mar. 29, 2022

(54) METHOD AND SYSTEM FOR CARDIAC HEALTH MONITORING

(71) Applicant: TEN3T HEALTHCARE PVT. LTD., Karnataka (IN)

(72) Inventors: Rahul Shingrani, Mumbai (IN); Sudhir Borgonha, Bangalore (IN)

(73) Assignee: TEN3T HEALTHCARE PVT. LTD., Bangalore (IN)

( * ) Notice: Subject to any disclaimer, the term of this patent is extended or adjusted under 35 U.S.C. 154(b) by 432 days.

(21) Appl. No.: 16/321,730

(22) PCT Filed: Jul. 27, 2017

(86) PCT No.: PCT/IB2017/054565
§ 371 (c)(1),
(2) Date: Jan. 29, 2019

(87) PCT Pub. No.: WO2018/020454
PCT Pub. Date: Feb. 1, 2018

(65) Prior Publication Data
US 2019/0159691 A1   May 30, 2019

(30) Foreign Application Priority Data
Jul. 29, 2016 (IN) .............................. 201641026129

(51) Int. Cl.
*A61B 5/024* (2006.01)
*A61B 5/00* (2006.01)
(Continued)

(52) U.S. Cl.
CPC ........ *A61B 5/02438* (2013.01); *A61B 5/0006* (2013.01); *A61B 5/0022* (2013.01);
(Continued)

(58) Field of Classification Search
None
See application file for complete search history.

(56) References Cited

U.S. PATENT DOCUMENTS 5,549,113 A * 8/1996 Halleck .............. G08B 21/0453
600/484
9,364,150 B2 6/2016 Sebelius et al.
(Continued)

FOREIGN PATENT DOCUMENTS

EP        3038523 A1    7/2016
WO     2016044933 A1    3/2016

*Primary Examiner* — Michael W Kahelin
(74) *Attorney, Agent, or Firm* — Maschoff Brennan

(57) ABSTRACT

A system for monitoring a cardiac health of a subject by measuring an indicator of the cardiac health of a subject is disclosed. In some embodiments, the system comprises a wearable device configured for being detachably attached to a thoracic region of the subject, the subject being ambulatory or at rest, a communication device and a network server. In one embodiment, the wearable device is configured for sensing and communicating at least one of the electrocardiogram signals and sensor data representing the one or more clinically relevant health parameters of the subject to the communication device. Further, the communication device is configured for communicating at least the electrocardiogram signal and the sensor data representing the one or more clinically relevant health parameters of the subject to the network server using a first communication channel and a second communication channel.

7 Claims, 5 Drawing Sheets

(51) Int. Cl.
*A61B 5/02* (2006.01)
*A61B 5/24* (2021.01)

(52) U.S. Cl.
CPC ............ *A61B 5/02* (2013.01); *A61B 5/02444* (2013.01); *A61B 5/24* (2021.01); *A61B 5/0024* (2013.01); *A61B 5/681* (2013.01)

(56) References Cited

U.S. PATENT DOCUMENTS

| | | | |
|---|---|---|---|
| 2010/0234714 A1* | 9/2010 | Mercier | A61B 5/7445 600/388 |
| 2013/0102871 A1* | 4/2013 | Sebelius | G16H 40/63 600/391 |
| 2016/0119812 A1* | 4/2016 | Owan | H04W 28/0268 370/230 |

* cited by examiner

METHOD AND SYSTEM FOR CARDIAC HEALTH MONITORING

FIELD OF THE INVENTION

The present disclosure relates to medical electronics and more particularly relates to a method and system for cardiac health monitoring.

BACKGROUND TO THE INVENTION

The dynamic growth of technology has played a significant role in automating most of the activities that are part of our daily life. One such field where technology has been employed for human aid is health management, where systems are used for monitoring, diagnosing, and treatment purposes. Medical electronics is a dedicated area of electronics which focuses on health management related systems.

Cardiac monitoring, wherein subject condition is assessed relative to their cardiac function, is a main focus of medical electronics systems. Systems that are employed in this domain collect data that represent state of health of subjects, and present this data to physicians or other qualified personnel for further analysis.

However, systems that are currently being used for the cardiac health monitoring purpose have certain disadvantages. First of all, conventional systems require user intervention at various stages of operation. Further, the existing cardiac monitoring systems collect data only upon detecting occurrence of a predefined event and hence miss other events of importance that are not predefined events. Some of the existing systems also require manual trigger for monitoring and recording the data, which means a caretaker or the subject himself needs to activate the system. Another disadvantage is that the existing systems collect data upon identifying occurrence of an event in isolation and hence miss a correlation with other events or conditions that may have a bearing on the event.

As is well known in the art, electrocardiograph (ECG) techniques monitor the electrical activity of the heart. A typical ECG tracing of the cardiac cycle (heartbeat) consists of a P wave, a QRS complex and a T wave. For ECG interpretation, the P, QRS and T waves are analysed in terms of amplitude, duration, intervals between peaks and valleys and changes over time. Very often, rhythm events do not occur continuously, but require long observation time (perhaps one or more days). For such observation, wearable ECG monitors (also called Holter monitors) are used, which collect ECG data, store the collected ECG data on-board the wearable device and the wearable device is collected from the subject for accessing and analysing the stored data. Further, some advanced wearable devices communicate the ECG data to a networked server through a wired or wireless communication channels. However, such communication often involves network related data drops and critical data may be lost during communication. Hence conventional systems fail to assure reliability and robustness of data transfer.

SUMMARY OF THE INVENTION

Thus there exists a need for a system and method which mitigates at least some of the disadvantages of the state of the art.

This summary is provided to introduce a selection of concepts in a simple manner that are further described in the detailed description of the disclosure. This summary is not intended to identify key or essential inventive concepts of the subject matter nor is it intended for determining the scope of the disclosure.

A system for monitoring a cardiac health of a subject by measuring an indicator of the cardiac health of a subject is disclosed. In some embodiments of the present disclosure, the system comprises a wearable device configured for being detachably attached to a thoracic region of the subject, the subject being ambulatory or at rest, a communication device and a network server. In one embodiment of the present disclosure, wearable device comprises one or more sensors including one or more electrostatic sensors for sensing at least an electrocardiogram signal of the subject, and a communication module for communicating sensor data from the one or more sensors to a communication device. In another embodiment, the one or more sensors comprise sensors for measuring one or more clinically relevant health parameters of the subject. In yet another embodiment, the communication device configured for receiving the sensor data from the wearable device and communicating the sensor data with a network server using a first communication channel and a second communication channel. In yet another embodiment, the network server being configured for receiving the sensor data from the communication device through the first communication channel and the second communication channel, processing the sensor data received from the first communication channel in real-time or near-real-time for performing one or more actions, comparing the sensor data received through the first communication channel and the second communication channel, storing the resulting sensor data, and processing the resultant sensor data for extracting information on the cardiac activity of the subject over a defined period of time.

In yet another embodiment of the present disclosure, the network server is further configured for processing the sensor data representing one or more clinically relevant health parameters of the subject and performing the one or more actions in real-time or near real-time, wherein the one or more actions comprise identifying a symptomatic event, notifying the symptomatic event to a pre-defined set of users and displaying the processed sensor data on a user device for viewing by a viewer. To further clarify advantages and features of the present disclosure, a more particular description of the disclosure will be rendered by reference to specific embodiments thereof, which is illustrated in the appended figures. It is to be appreciated that these figures depict only typical embodiments of the disclosure and are therefore not to be considered limiting of its scope. The disclosure will be described and explained with additional specificity and detail with the accompanying figures.

BRIEF DESCRIPTION OF THE FIGURES

The disclosure will be described and explained with additional specificity and detail with the accompanying figures in which.

Figure 1:
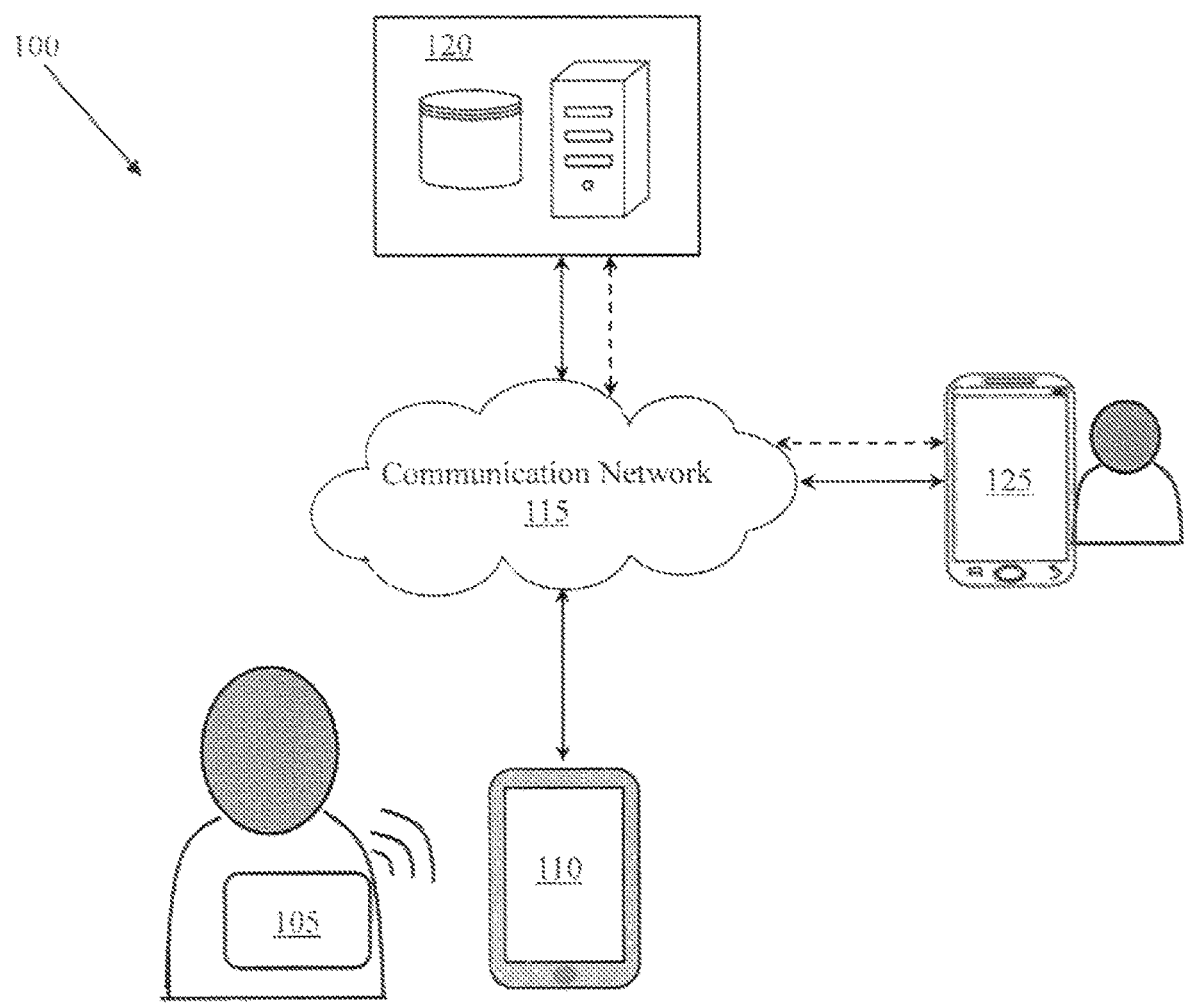
FIG. 1 is a block diagram of an exemplary system for monitoring cardiac health of a subject in accordance with an embodiment of the present disclosure.

Further, persons skilled in the art to which this disclosure belongs will appreciate that elements in the figures are illustrated for simplicity and may not have necessarily been drawn to scale. Furthermore, in terms of the construction of the device, one or more components of the device may have been represented in the figures by conventional symbols, and the figures may show only those specific details that are pertinent to understanding the embodiments of the present disclosure so as not to obscure the figures with details that will be readily apparent to those of ordinary skill in the art having benefit of the description herein.

DESCRIPTION OF THE INVENTION

For the purpose of promoting an understanding of the principles of the disclosure, reference will now be made to the embodiment illustrated in the figures and specific language will be used to describe them. It will nevertheless be understood that no limitation of the scope of the disclosure is thereby intended. Such alterations and further modifications to the disclosure, and such further applications of the principles of the disclosure as described herein being contemplated as would normally occur to one skilled in the art to which the disclosure relates are deemed to be a part of this disclosure.

It will be understood by those skilled in the art that the foregoing general description and the following detailed description are exemplary and explanatory of the disclosure and are not intended to be restrictive thereof.

The terms "comprises", "comprising", or any other variations thereof, are intended to cover a non-exclusive inclusion, such that a process or method that comprises a list of steps does not include only those steps but may include other steps not expressly listed or inherent to such a process or a method. Similarly, one or more devices or sub-systems or elements or structures or components preceded by "comprises . . . a" does not, without more constraints, preclude the existence of other devices, other sub-systems, other elements, other structures, other components, additional devices, additional sub-systems, additional elements, additional structures, or additional components. Appearances of the phrase "in an embodiment", "in another embodiment" and similar language throughout this specification may, but do not necessarily, all refer to the same embodiment.

Unless otherwise defined, all technical and scientific terms used herein have the same meaning as commonly understood by one of ordinary skill in the art to which this disclosure belongs. The system, methods, and examples provided herein are illustrative only and not intended to be limiting.

Embodiments of the present disclosure will be described below in detail with reference to the accompanying figures.

The embodiments herein disclose a method and system for monitoring cardiac health of a subject in real-time or near real-time by measuring an indicator of the cardiac health of the subject. In one embodiment of the present disclosure, the system comprises a wearable device, a communication device and a network server, wherein the wearable device comprises one or more sensors including one or more electrostatic sensors for sensing at least an electrocardiogram signal of the subject, when detachably attached to a thoracic region of the subject. Further, the one or more sensors comprise sensors for monitoring clinically relevant health parameters of the subject. The sensor data is communicated to the communication device preferably using short range communication such as Bluetooth. In another embodiment of the present disclosure, the communication device communicates the received sensor data to the network server through a first communication channel and a second communication channel, wherein the first communication channel is a non-reliable communication channel and the second communication channel is a reliable communication channel.

The first communication channel ensures minimal lag for real-time processing and display of the sensor data and the second communication channel ensures that any dropped sensor data (data packets) find their final resting location on a database associated with the network server. The network server stores or organizes the sensor data received through the first communication channel and the second communication channel separately in a database.

In one embodiment of the present disclosure, the network server (preferably a cloud server) processes the sensor data received through the first communication channel in real-time or near real-time for performing one or more actions. That is, the network server generates an electrocardiogram signal based on the sensor data received from the first communication channel and analyses the cardiogram signal to determine one or more parameters. Then the network server performs one or more actions in real-time or near real-time, wherein the one or more actions include but not limited to identifying a cardiac event, notifying the cardiac event to a pre-defined set of users and displaying the electrocardiogram signal on a user device for viewing by a viewer.

Further, the network server processes the sensor data received through first communication channel and the second communication channel, wherein the processing comprises, comparing the sensor data received through the first communication channel and the second communication channel, storing the resulting sensor data, wherein the resultant sensor data comprises all the data packets set by the communication device, and processing the resultant sensor data for extracting information on the cardiac activity of the subject over a defined period of time. That is, the network server identifies the missing sensor data (data packets) by comparing sensor data received from the first communication channel and the second communication channel, and generates resultant sensor data. Then the network server generates an electrocardiogram signal based on the resultant sensor data, extracts one or more parameters from the generated electrocardiogram signal. Further, the network server determines one or more cardiac events, a pattern in a variation of the electrocardiogram signals over time, a statistical mean and standard deviation of one or more parameters of the electrocardiogram signals, and correlation between the activity and stance of the subject.

Hence, the system provides cardiac health data of the subject in real-time or near real-time to any pre-defined user(s) wherein the user may be a doctor or a hospitalist or to any person in charge of a patient (subject). Further, the system stores resultant sensor data for performing analytics on historical data, thereby enabling robust analysis.

FIG. 1 is a block diagram of an exemplary system for monitoring cardiac health of a subject in accordance with an embodiment of the present disclosure. As shown, the system 100 comprises a wearable device 105, a communication device 110, a communication network 115, a network server 120 and a user device 125. In one embodiment of the present disclosure, the wearable device 105 is communicatively connected to the communication device 110 using near field communication technology, and the communication device 110, the network server 120 and the user device 125 are communicatively connected via the communication network 115.

The wearable device 105 is configured for being detachably attached to a thoracic region of a subject, the subject being ambulatory or at rest. In one embodiment of the present disclosure, the wearable device 105 comprises one or more sensors configured for measuring electrocardiogram signal of the subject and one or more of physiological and physical parameters of the subject such as but not limited to blood pressure, oxygen saturation in the blood of the subject, activity of the subject, stance, temperature, etc.

In a preferred embodiment of the present disclosure, the wearable device 105 comprises one or more electrostatic sensors for sensing at least an electrocardiogram signal of the subject. For example, the wearable device 105 may include three sensors (3 electrodes) for generating three bipolar leads and three augmented leads for measuring electrical activity of the heart over a period of time. However, the wearable device 105 may be configured to generate 5-lead or 12-lead electrocardiogram (ECG) signal. In one implementation, each sensor is a dry sensor, i.e., the sensors does not require a silicone gel or any conductive gel for their reliable operation in sensing the ECG signal. The wearable device 105 further comprises a controller for processing and communicating the sensor data to the communication device and storage means for storing the sensor data and associated secondary information temporarily, wherein the storage means may be any one of a RAM, a ROM, or a Flash memory device.

The communication device 110 may be one of a smartphone, tablet, personal digital assistant, and the like. In one embodiment of the present disclosure, the communication device 110 is configured to communicate with the wearable device 105 for receiving the sensor data and the network server 120 to communicate the sensor data using at least one wired or wireless communication channel. For example, the communication device 110 may configured to communicate with the wearable device 105 using wireless technologies such as Bluetooth, Wi-Fi, ANT, ANT+, etc. In a preferred embodiment, the communication device 110 communicates with the wearable device 105 using Bluetooth. Further, the communication device 110 is configured to communicate with the network server 120 through the communication network 115 in one or more ways such as wired, wireless connections or a combination thereof. It will be appreciated by those skilled in the art that the communication device 210 includes one or more processors for processing data, one or more memory units for instructions and data storage and other known functional units enabling communication between the communication device 110 and the network server 120 for data exchange. It will be appreciated by those skilled in the art that the communication device 110 comprises one or more processors for processing sensor data, one or more memory units for instructions and data storage. Further, the communication device 110 comprises one or more communication units and SDKs enabling communication with the wearable device 105 and the network server 120 for sensor data exchange.

The communication network 115 may be one of the different types of networks, such as intranet, local area network (LAN), wide area network (WAN), the internet, and the like. The communication network 115 may either be a dedicated network or a shared network. The shared network represents an association of the different types of networks that use a variety of protocols, for example, Hypertext Transfer Protocol (HTTP), Transmission Control Protocol/Internet Protocol (TCP/IP), Wireless Application Protocol (WAP), and the like. Further the communication network 115 may include a variety of network devices, including routers, bridges, servers, modems, computing devices, storage devices, and the like. In one implementation, the communication network 115 is the internet which enables communication between the communication device 110, the network server 120 and the user device 125.

The network server 120 may be one of a computer server or a network of computers or a virtual server which provides functionalities or services for other programs or devices such as for the communication device 110 and the user device 125. In one implementation, the network server 120 is a cloud server comprising one or more processors, associated processing modules, interfaces and storage devices communicatively interconnected to one another through one or more communication means for communicating information. The storage devices within the network server 120 may include volatile and non-volatile memory devices for storing information/data and instructions to be executed by the one or more processors and for storing temporary variables or other intermediate information during processing.

In one embodiment of the present disclosure, the network server 120 receives the sensor data from the communication device 110 through a first communication channel and a second communication channel. The sensor data received through the first communication channel and the second communication channel are recorded or organized separately in a database (preferably SQL database) using custom APIs. Further, the network server 120 hosts an algorithm customized for sensor data processing and performing the one or more actions in real-time or near real-time, wherein the one or more actions comprise identifying a cardiac event, notifying the cardiac event to a pre-defined set of users, for example, a physician, caretaker, family, friends or any such person, and displaying the electrocardiogram signal on one or more user devices (for example user device 125) for viewing by the user. The manner in which the network server 120 receives the sensor data, processes the sensor data and performs the one or more actions in real-time or near real-time is explained in detail further in the present disclosure.

The user device 125 may be one of a smartphone, tablet, personal digital assistant, laptop, and the like. In one embodiment of the present disclosure, the user device 125 is configured to communicate with the network server 120 using at least one wired or wireless communication channel. Typically, the user device 125 may be any electronic communication device associated with the user (a physician, caretaker, hospitalist or any person) using which the user may access data stored in the network server 120. It has to be noted that the access to the network server 120 and hence to the data stored in the network server 120 is limited to each individual user or set of users and the same may be defined by an administrator or an authorized person of the system 100. For example, physician(s) may be provided with complete access to the network server 120, i.e., the physician(s) may receive notification sent by the network server 120, the physician(s) may login to the network server 120 to manage data, as well as control settings, and to view and analyse data. However, a caretaker may have limited access, for example, the user device associated with the caretaker may only receive notification sent by the network server 120. In one embodiment of the present disclosure, a client application may be provided which provides an interface for the physician(s) to access and manage data stored in the network server 120. The data as described herein refers to at least one of sensor data, ECG signal, parameters associated with the ECG signal, physical or physiological parameters, etc.

Figure 2A:
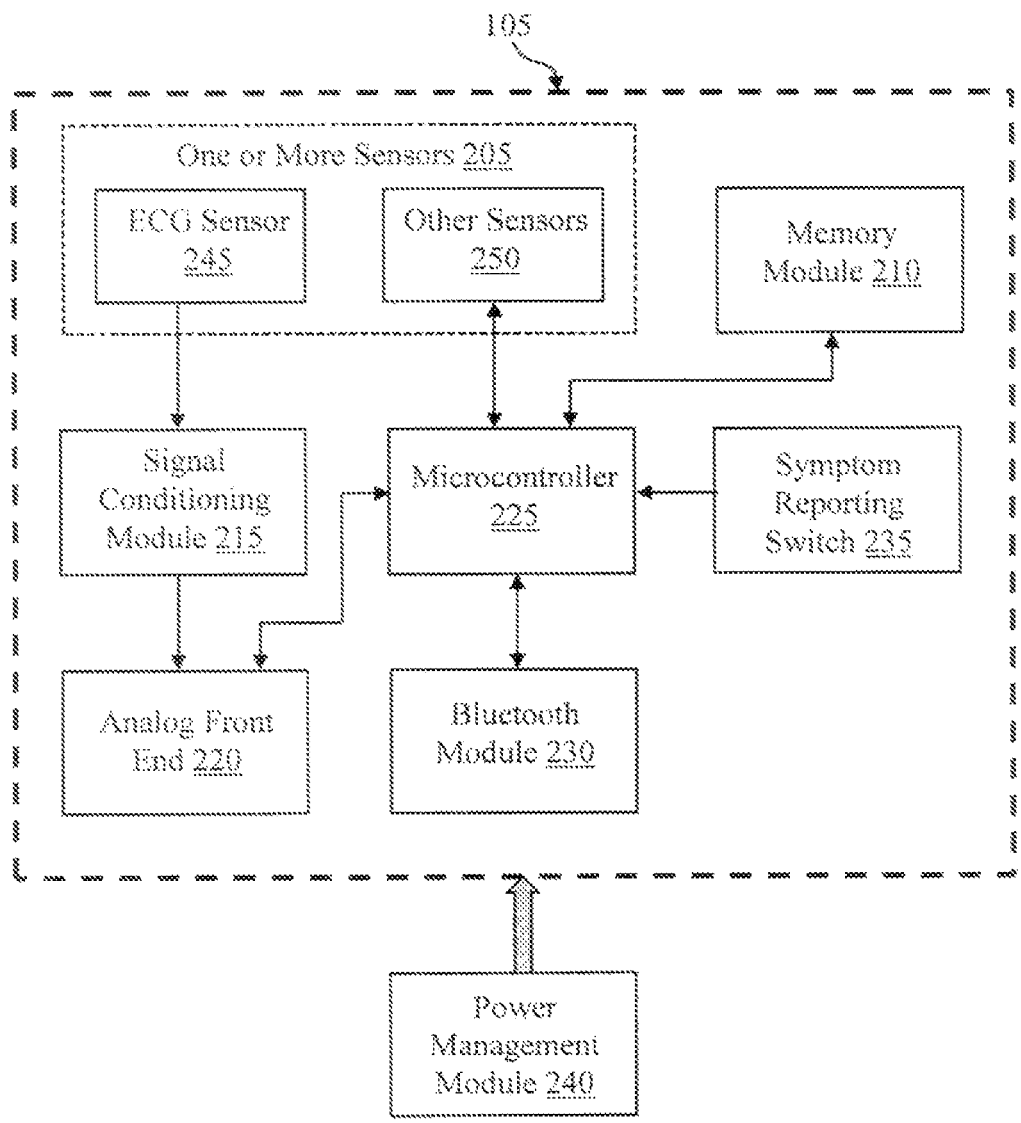
FIG. 2A is a block diagram of an exemplary wearable device in accordance with an embodiment of the present disclosure.

FIG. 2A is a block diagram of an exemplary wearable device in accordance with an embodiment of the present disclosure. As shown, the wearable device 105 comprises one or more sensors 205, a memory module 210, a signal conditioning module 215, an analog front end 220, a microcontroller 225, a Bluetooth module 230, one or more symptom reporting switches 235 and a power management module 240.

In one embodiment of the present disclosure, the one or more sensors 205 comprises an electrocardiograph (ECG) sensor 245 (or one or more electrostatic sensors) for sensing at least an electrocardiogram signal of the subject and other sensors 250 configured for measuring one or more of physiological and physical parameters (clinically relevant health parameters) of the subject from a group of parameters comprising, but not limited to, blood pressure, oxygen saturation in the blood of the subject, activity of the subject, stance, temperature, etc. In a preferred embodiment of the present disclosure, an ultra-high impedance solid state dry contact ECG sensor is used for measuring the ECG signal of the subject.

The memory module 210 may include any known storage means for storing the sensor data and associated secondary information temporarily, wherein the storage means may be any one of a RAM, a ROM, or a Flash memory device. Further, the memory module 210 stores information/data and instructions to be executed by the microcontroller 225 and may store temporary variables or other intermediate information during processing.

In one embodiment of the present disclosure, the signal conditioning module 215 filters the ECG signal (sensor data) measured by the ECG sensor 245 and hence removes unwanted frequencies and breathing muscle artefacts, if any. Further, the signal conditioning module 215 is configured to amplify the received ECG signal. In other words, the signal conditioning module 215 manipulates the ECG signal to meet the requirement of the next stage of processing by the analog front end 220.

The analog front end 220 converts the analog signal received from the signal conditioning module 215 to digital signal which is fed to the microcontroller 225 for further processing. The analog front end 220 may include one or more of a instrumentation amplifiers, dc blocking filters, gain amplifiers, anti-aliasing filters and analog to digital converter configured for converting the analog signal to the digital signal.

The microcontroller 225 may be one of a general purpose microcontroller, a digital signal processor or a dedicated controller (ASIC) configured for processing the sensor data. In one embodiment of the present disclosure, the microcontroller 225 receives sensor data from the analog front end 220 and generates data packets suitable for transmission, wherein the each data packet comprises sensor data and control information including unique packet identifier (packet ID). Thus generated data packets comprising the sensor data are communicated to the communication device 110 using the Bluetooth module 230. In some other implementations, the data packets may be communicated using any known wireless technology. The wireless communication offers the added advantage that the subject may move around without any hindrance.

In some implementation, the microcontroller is further configured to receive and process the data from other sensors 250, wherein the other sensors may include but not limited to a body temperature sensor, peripheral capillary oxygen saturation ($SPO_2$) sensor for measuring the amount of oxygen in the blood, an accelerometer, etc. Thus processed other sensor data is communicated to the communication device 110 using the Bluetooth module 230.

In one embodiment of the present disclosure, the one or more symptom reporting switches 235 are provided on the wearable device 105 using which the patient may trigger alerts or send notifications to the doctors, hospitalists or any caretaker (user) during an emergency. Upon activating the switch, the wearable device 105 triggers the communication device 110 which is turn sends the notifications to the user device 125 associated with the user.

The power management module 240 comprises one or more rechargeable batteries that power the wearable device 105. In one embodiment of the present disclosure, the power management module 220 may be configured to generate energy from mechanical movements of the patient/subject to charge the one or more re-chargeable batteries that powers the wearable device 105.

Hence, the wearable device 105 comprising the one or more sensors measures at least one of the electrocardiogram signal of the subject and one or more clinically relevant health parameters of the subject. Further, the wearable device 105 processes the sensor data and communicates the sensor data to the communication device 110 via the Bluetooth. The manner in which the system 100 monitors the cardiac health of a subject by measuring an indicator of the cardiac health of the subject is described in detail further below. The indicator as described herein refers to the one or more sensor data including at least one of the ECG signal and other sensor data.

Figure 2B:
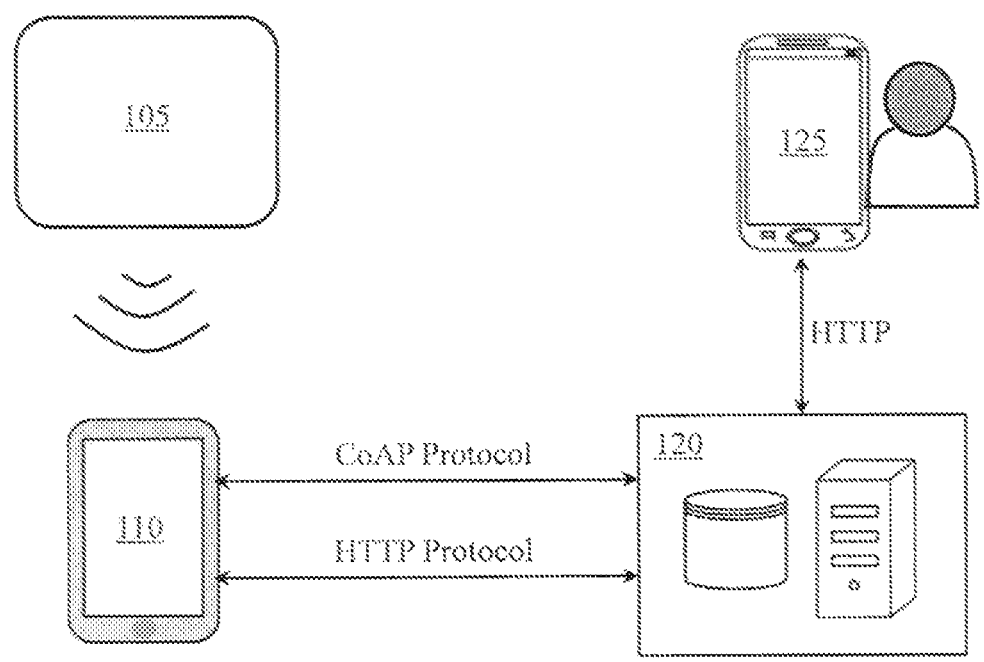
FIG. 2B is a block diagram of the system specifically illustrating the sensor data communication in accordance with an embodiment of the present disclosure.

FIG. 2B is a block diagram of the system specifically illustrating the sensor data communication in accordance with an embodiment of the present disclosure.

As described, the wearable device 105 measures at least one of the ECG signals of the subject and one or more clinically relevant health parameters of the subject. Referring to FIG. 2B, the wearable device 105 communicates the sensor data comprising at least one of the ECG signals and other sensor data representing the one or more clinically relevant health parameters of the subject to the communication device 110 preferably via Bluetooth.

In one embodiment of the present disclosure, the communication device 110 communicates the sensor data received from the wearable device 105 to the network server 120 using a first communication channel and the second communication channel as shown through the communication network 115 (not shown), wherein the first communication channel is a reliable communication channel (fast channel) and the second communication channel is a non-reliable communication channel (slow channel).

In a preferred embodiment of the present disclosure, the first communication channel is a CoAP channel, wherein the sensor data is communication in real-time or near real-time ensuring minimal lag and the second communication channel is a HTTP channel which ensures complete data transmission without any loss. In embodiment, the communication device 110 communicates the sensor data (data packets) in real-time using CoAP channel and temporarily stores the senor data in a local memory. It has to be noted that the communication device 110 may be configured to resend the sensor data using the CoAP channel for a user specified number of retry events. Upon communicating the sensor data using CoAP channel, the communication device 110 communicates the sensor data to the network server 120 using HTTP channel. That is, HTTP post service routinely checks for the sensor data stored in the communication device 110 and transfers all the senor data (data packets) to the network server 120. Upon receiving sensor data reception acknowledgment from the network server 120, the sensor data is deleted from the local memory of the communication device 110. However, the sensor data may be communicated using both CoAP and HTTP channel simultaneously. In an alternate embodiment, the communication device 110 may be configured to display the ECG signal on a display module associated with the communication device 110. The manner in which the network server 120 processes sensor data is described in detail further below.

In various embodiments, operations and functionalities of the wearable device 105 and hence the sensor module 205 may be remotely controlled. A few examples of functionalities of the one or more sensors that may be controlled remotely include activation of monitoring and data collection, termination of monitoring and data collection, detection of peeling off of the one or more sensors or the wearable device 105, configuration of the wearable device 105, wherein the configuration refers to configuration of parameters such as sampling rate, gain, bandwidth, filter options, etc.

Figure 3:
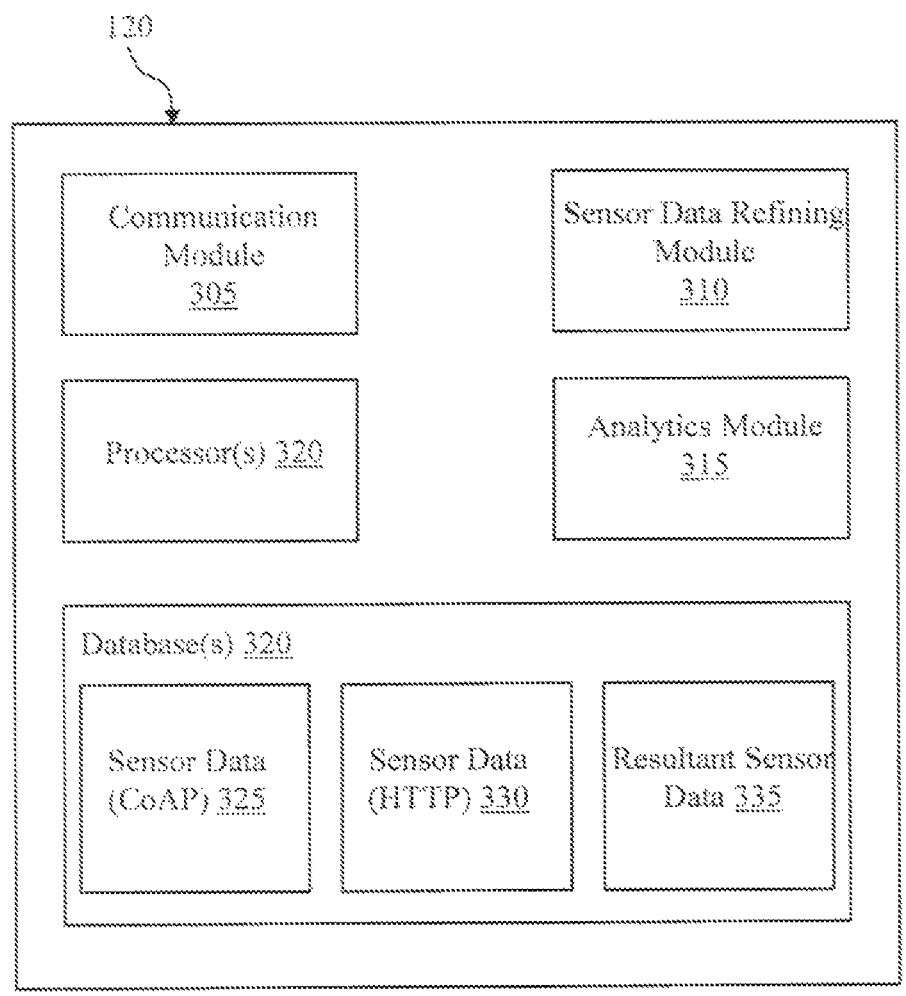
FIG. 3 illustrates an exemplary block diagram of the network server 120 in accordance with an embodiment of the present disclosure.

FIG. 3 illustrates an exemplary block diagram of the network server 120 in accordance with an embodiment of the present disclosure. As shown, the network server 120 (server) comprises a communication module 305, a sensor data refining module 310, an analytics module 315, processor(s) 320 and a database(s) 325. The communication module 305 enables communication between the communication device 110, user device 125 and the network server 120. As described in FIG. 2B, the network server 120 receives the sensor data using the first and the second communication channels, wherein the sensor data may include at least one of the ECG sensor data (ECG signal of the subject) and other sensor data representing the one or more clinically relevant health parameters of the subject. . In one embodiment of the present disclosure, the sensor data 325 received using the first communication channel (for example, CoAP) and the second communication channel (for example, HTTP) are separately stored in the database 320 using customer APIs, as shown, sensor data 325 and sensor data 330.

In one embodiment of the present disclosure, the analytics module 315 processes the received sensor data, wherein the sensor data received using the first communication channel (sensor data 325 received using CoAP) is processed in real-time or near real-time for performing one or more actions in real-time or near real-time. That is, the analytics module 315 generates the electrocardiogram signal from the sensor data 325 and analyses the generated cardiogram signal to determine one or more parameters, wherein the one or more parameters may include QRS complexes, P-R interval, S-T interval, etc. Thus generated cardiogram signal and the determined one or more parameters are displayed in real-time or near real-time on the user device 125 for viewing by the user. In another embodiment of the present disclosure, values of the one or more determined parameters are compared with pre-defined thresholds to identify a cardiac event and upon occurrence of any event, the same is notified to a pre-defined set of users, for example, to a physician, hospitalist, caretaker, etc.

In another embodiment of the present disclosure, the sensor data refining module 310 generates a resultant sensor data 335, wherein the resultant sensor data 335 comprises all the data packets including data packets missed during non-reliable communication, i.e., CoAP communication. In some implementations, the sensor data refining module 310 compares the sensor data 325 (received using first communication channel, CoAP) and the sensor data 330 (received using second communication channel, HTTP) and deletes the duplicate data packets to generate the resultant sensor data 335. Hence any dropped data packets during CoAP communication find their final resting location on the database 320.

In one embodiment of the present disclosure, the analytics module 315 processes the resultant data 335 for extracting information on the cardiac activity of the subject over a time pre-defined time period. That is, the analytics module 315 generates an electrocardiogram signal based on the resultant sensor data 335 and extracts one or more parameters from the generated cardiogram signal, wherein the one or more parameters may include QRS complexes, P-R interval, S-T interval, etc. It has to be noted that the QRS complexes may be determined or extracted using any known algorithms from the field of artificial neural networks, genetic algorithms, wavelet transforms or filter bank approaches, adaptive threshold techniques, etc.

Thus generated cardiogram signal and associated one or more parameters are stored in the database 320 for future reference and analysis by the user. In another embodiment of the present disclosure, the analytics module 315 is further configured for determining one or more of a cardiac event, a pattern in a variation of the electrocardiogram signals over time, a statistical mean and standard deviation of one or more parameters of the electrocardiogram signals, and correlation between the activity and stance of the subject, etc. Further, based on the cardiac event, the analytics module 315 may perform one or more actions, wherein the one or more actions may include but not limited to, notifying the cardiac event to the pre-defined set of users and displaying the electrocardiogram signal on the user device for viewing by a viewer, etc. In one embodiment of the present disclosure, the functionalities of the sensor data refining module 310 and the analytics module 315 may be implemented on one or more processors 320.

It has to be noted that the other sensor data (representing the one or more clinically relevant health parameters of the subject) is stored independently in the database 320 and processed to identify various physiological and physical parameters of the subject from a group of parameters comprising, but not limited to, blood pressure, oxygen saturation in the blood of the subject, activity of the subject, temperature, stance, etc. For example, measured values of the clinically relevant parameters (for example, blood pressure value) are compared with pre-defined threshold values to identify one or more symptomatic events and upon occurrence of any such event, the same is notified to a pre-defined set of users, for example, to a physician, hospitalist, caretaker, etc. In some implementations, the values of the one or more clinically relevant parameters are communicated to the user device along with the ECG signal. For example, variation in oxygen level in blood may be indicative of a cardiac event and may indicate the need for supplemental oxygen. Hence, the values indicating the oxygen level may be displayed on the user device 125 along with the ECG signal.

In some implementations, the network server 120 is further configured to host at least one mechanism and associated hardware and software means for detecting peeling off of the one or more sensor of the wearable device 105 or the loss of contact between the one or more sensors and the body of the subject. The network server 120 may also be configured to stop/pause data recording, upon detecting the peeling off of the one or more sensors, or any other case which results in which the network server 120 not receiving sensor data from the communication device 110, for more than a predefined time period.

In some other implementations, the network server 120 comprises at least one suitable User Interface (UI), preferably a Graphical User Interface (GUI) (not shown) for the physician or any authorized person to access data stored in the network server 120. The physician or any authorized person may interact with cardiac health monitoring system 100 through the GUI or through the user device 125 for configuring necessary settings and/or alerts required to manage the cardiac monitoring process in a desired manner. The UI or GUI may allow the user to customize the way the sensor data is presented at the backend, for further analysis. In an embodiment, the GUI may provide option for the physician and/or any such authorized person to login to the cardiac health monitoring system 100 to manage sensor data, as well as control settings, and to view and analyse sensor data.

As described, the network server 120 is configured for receiving the sensor data using the first non-reliable communication channel and the second reliable communication channel. The sensor data received using first non-reliable communication channel is processed in real-time or near-real-time and the result of processing is provided to the user in real-time or near-real-time. This enables real-time or near-real-time plotting of ECG data on the user device 125. However, in the real-time plotting, it is acceptable to occasionally lose data packets and this is displayed using a blank space between a continuous signals. However, such data may be critical during detailed analysis by the network server 120 or by the users. Hence, the network server 120 identifies the missing data packets in the non-reliable communication by comparing the data packets received using first and the second communication channel and generates the resultant sensor data which may be processed further to provide detailed analytics. This assures reliability and robustness of data transfer between the wearable device 105 and the network server 120.

In various embodiments, the network server 120 may be configured to provide all collected sensor data, processed data, or only selected portions of the sensor data or processed data (which shows the detected anomaly) to the user, as pre-configured. The network server 120 may be further configured to have at least one of the additional features mentioned below:

Predictive Analysis

The predictive analysis feature may allow the network server 120 to predict, by processing sensor data being collected from the subject, likelihood of occurrence of any adverse cardiac event within a specific time period. The network server 120 may use suitable pattern forming and pattern matching algorithms for this purpose.

Activity Correlation

The network server 120 may, with the help of an embedded activity monitor, collect information pertaining to various activities (detected by one or more sensors) the subject is involved in, while being monitored. Further, by mapping the cardiac data with corresponding activity, the network server 120 may help the physician to understand which activity results in a particular health state of the subject.

Collaborative Diagnosis

The collaborative diagnosis feature may help the network server 120 to provide the physician to collaborate with other professionals, share subject data, and do online diagnosis of the subject's health condition. The collaboration feature may also provide a social sharing platform where experts may discuss cases and seek support to efficiently diagnose medical condition of subjects.

Figure 4:
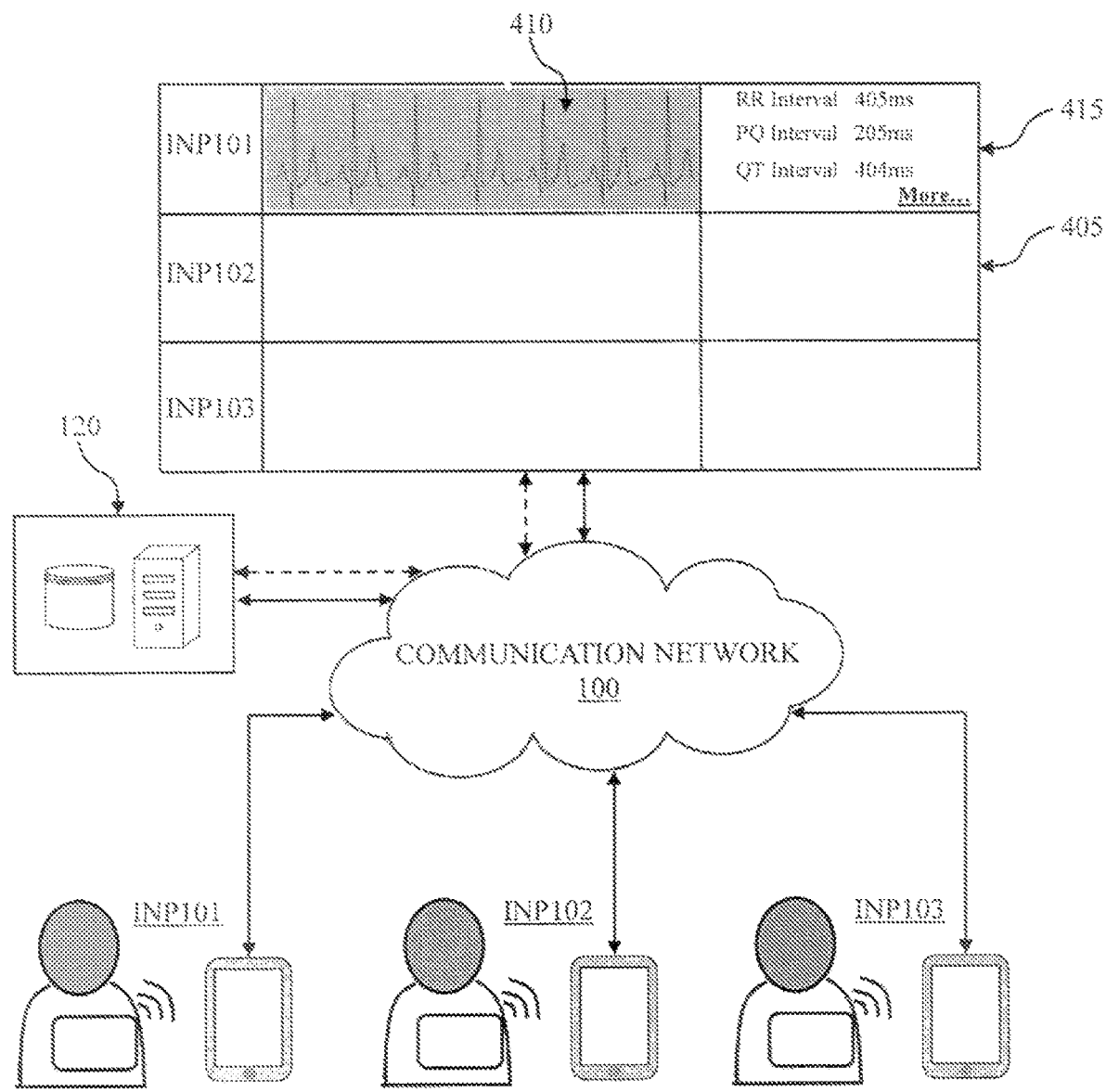
FIG. 4 illustrates an exemplary deployment of the system in a hospital environment in accordance with an embodiment of the present disclosure.

FIG. 4 illustrates an exemplary deployment of the system in a hospital environment in accordance with an embodiment of the present disclosure. In one embodiment, a single interface (dashboard) 405 may be provided for monitoring cardiac health of plurality of patients INP101, INP102, INP 103, etc. During such implementations, the sensor data of each patient among the plurality of patients are communicated to the network server 120 through the communication device using the first and second communication channel. It has to be noted that each patient and the sensor data associated with each patient may be identified based the communication device ID or a unique ID associated with the wearable device 105. The network server 120 processes the sensor data received using the first communication channel and displays on the user interface 405 in real-time or near-real-time, wherein the processed data comprises cardiac signal 410, one or more parameters 415, etc., as shown. Further, the network server 120 generates resultant data, processes the resultant data and stores in the database for future reference and analysis as described. Hence, a hospitalist or a physician may monitor cardiac health of the plurality of the patients simultaneously on a single screen.

While specific language has been used to describe the disclosure, any limitations arising on account of the same are not intended. As would be apparent to a person skilled in the art, various working modifications may be made to the method in order to implement the inventive concept as taught herein.

The figures and the foregoing description give examples of embodiments. Those skilled in the art will appreciate that one or more of the described elements may well be combined into a single functional element. Alternatively, certain elements may be split into multiple functional elements. Elements from one embodiment may be added to another embodiment. For example, orders of processes described herein may be changed and are not limited to the manner described herein. Moreover, the actions of any flow diagram need not be implemented in the order shown; nor do all of the acts necessarily need to be performed. Also, those acts that are not dependent on other acts may be performed in parallel with the other acts. The scope of embodiments is by no means limited by these specific examples. Numerous variations, whether explicitly given in the specification or not, such as differences in structure, dimension, and use of material, are possible. The scope of embodiments is at least as broad as given by the following claims.

The invention claimed is:

1. A system for monitoring a cardiac health of a subject by measuring an indicator of the cardiac health of the subject, the system comprising:
   a wearable device configured for being detachably attached to a thoracic region of the subject, the subject being ambulatory or at rest, wherein the wearable device comprises:
   one or more sensors comprising one or more electrostatic sensors for sensing at least an electrocardiogram signal of the subject; and
   a communication module;
   a communication device, wherein the communication module is configured to communicate sensor data from the one or more sensors to the communication device; and a network server, wherein the communication device is configured to receive the sensor data from the wearable device and communicate the sensor data to the network server through a first communication channel and a second communication channel, wherein the first communication channel is a CoAP channel and the second communication channel is a HTTP channel, wherein the network server being configured for:
receiving the sensor data from the communication device through the first communication channel and the second communication channel;
processing the sensor data received through the first communication channel in real-time or near-real-time for performing one or more actions;
comparing the sensor data received through the first communication channel and the second communication channel to generate resultant sensor data, wherein the resultant sensor data comprise all data packets including data packets missed during non-reliable communication through the first communication channel, wherein the first communication channel is a non-reliable communication channel configured to transmit the sensor data to ensure a minimal lag for the real-time or the near-real-time processing of the sensor data and the second communication channel is a reliable communication channel configured to transmit the sensor data to ensure the data packets missed during the non-reliable communication through the first communication channel are transmitted to the network server;
storing the resultant sensor data; and
processing the resultant sensor data for extracting information on the cardiac activity of the subject over a defined period of time.

2. The system of claim 1, wherein the one or more electrostatic sensors are disposed on a face of the wearable device, for being in direct contact with the thoracic region of the subject when detachably attached to the subject, for sensing electrocardiogram signals of the subject.

3. The system of claim 1, wherein the one or more sensors are configured for measuring one or more of physiological and physical parameters of the subject from a group of parameters comprising blood pressure, Oxygen Saturation in blood of the subject, activity of the subject, temperature, and stance.

4. The system of claim 1, wherein the wearable device further comprises a signal processing means for processing the sensor data, wherein the signal processing means comprises one or more of devices from a group comprising a microcontroller, a digital signal processor, and an ASIC.

5. The system as claimed in claim 1, wherein the network server further comprises:
one or more databases for storing the sensor data received from the communication device through the first communication channel and the second communication channel; and a processor configured for:
generating the electrocardiogram signal based on the sensor data received from the first communication channel;
determining one or more parameters by analysing the electrocardiogram signal; and
performing the one or more actions in real-time or near real-time, wherein the one or more actions comprise identifying a cardiac event, notifying the cardiac event to a pre-defined set of users, and displaying the electrocardiogram signal on a user device for viewing by a viewer.

6. The system of claim 1, wherein the processing of the resultant sensor data comprises:
generating the electrocardiogram signal based on the resultant sensor data;
extracting one or more parameters from the generated electrocardiogram signal; and
determining one or more of a cardiac event, a pattern in a variation of the electrocardiogram signal over time, a statistical mean, and a standard deviation of the one or more parameters of the electrocardiogram signal, and correlation between an activity and a stance of the subject.

7. The system as claimed in claim 1, wherein the network server is further configured for:
processing the sensor data representing one or more clinically relevant health parameters of the subject; and
performing the one or more actions in real-time or near real-time, wherein the one or more actions comprise identifying a symptomatic event, notifying the symptomatic event to a pre-defined set of users,. and displaying processed sensor data on a user device for viewing by a viewer.

* * * * *